(12) United States Patent
Fahy et al.

(10) Patent No.: US 8,815,899 B1
(45) Date of Patent: Aug. 26, 2014

(54) NUTRITIONAL ACTIVATION OF TELOMERASE IN VITRO AND IN VIVO WITH INCREASED SAFETY

(75) Inventors: Gregory M. Fahy, Norco, CA (US); Lancer Brown, Reno, NV (US)

(73) Assignee: Intervene Biomedical, Norco, CA (US)

( * ) Notice: Subject to any disclaimer, the term of this patent is extended or adjusted under 35 U.S.C. 154(b) by 0 days.

(21) Appl. No.: 13/420,272

(22) Filed: Mar. 14, 2012

Related U.S. Application Data

(60) Provisional application No. 61/452,592, filed on Mar. 14, 2011.

(51) Int. Cl.
*A01N 43/42* (2006.01)
*A61K 31/47* (2006.01)

(52) U.S. Cl.
USPC ........................................ 514/310

(58) Field of Classification Search
None
See application file for complete search history.

(56) References Cited

U.S. PATENT DOCUMENTS

| | | | |
|---|---|---|---|
| 7,504,376 B2 * | 3/2009 | Harris et al. | 514/1.1 |
| 2009/0209487 A1 * | 8/2009 | Brown | 514/62 |
| 2012/0045426 A1 * | 2/2012 | St. Cyr et al. | 424/94.64 |

* cited by examiner

*Primary Examiner* — Dennis Heyer
*Assistant Examiner* — Daniel M Podgorski
(74) *Attorney, Agent, or Firm* — Stout, Uxa & Buyan, LLP; Donald E. Stout

(57) ABSTRACT

A nutritional composition and method is provided in which telomerase expression can be safely activated in living cells. The nutritional composition can induce TERT mRNA or h-TERT mRNA and telomerase in vitro and in vivo while at the same time inhibiting potential side effects, helping to prevent certain types of cancer, and slowing the growth of any cancer cells that may exist in vivo. The method entails exposing cells to L-carnosine concentrations in the range of 51-100 mM or to a combination of L-carnosine and L-fucose in which the concentration of L-carnosine is 30-100 mM and the concentration of L-fucose is in the range from 0.1 micromolar to 100 mM.

20 Claims, 8 Drawing Sheets

ATP levels in the third in vitro experiment.

NUTRITIONAL ACTIVATION OF TELOMERASE IN VITRO AND IN VIVO WITH INCREASED SAFETY

CROSS-REFERENCE TO RELATED APPLICATIONS

This application claims from the benefit of U.S. Provisional Application No. 61/452,592, filed on Mar. 14, 2011 and entitled NUTRITIONAL ACTIVATION OF TELOMERASE IN VITRO AND IN VIVO WITHOUT INCREASED CANCER RISK, the entire contents of which are hereby incorporated by reference.

BACKGROUND OF THE INVENTION

Aging on the cellular level involves many paradoxes. On the one hand, many biochemical changes have been documented that suggest a variety of mechanisms of cellular aging. On the other hand, the simple expedient of increasing the expression of the enzyme telomerase is well known to rejuvenate cells and allow them to survive indefinitely and to function normally for an unlimited time [1]. Telomerase is a ribonucleoprotein consisting of 2 subunits, an RNA template component for nucleotide incorporation (TR; referred to as h-TR in humans) and a catalytic protein component (telomerase reverse-transcriptase, or TERT, which is referred to as h-TERT when it is the human version) whose combined primary function is to prevent telomere shortening and to repair and otherwise maintain telomere integrity. Therefore, it is reasonable to conclude that the primary problem of preventing and reversing aging on the level of dividing cells is to maintain healthy telomeres, and that the molecular mechanisms often thought to drive aging on a cellular level are actually either side effects of telomere shortening or drivers of telomere shortening or damage that can be overcome by telomerase induction.

Telomeres are the repetitive segments of DNA found at the ends of all chromosomes. Because of the way DNA is copied by DNA polymerase, the end of a given DNA strand cannot be fully replicated by the polymerase, which leads to a loss of DNA from the end of the replicated DNA strand every time a cell's DNA is copied during the S-phase of the cell division cycle. The failure of DNA polymerase to copy the complete DNA strand is referred to as the "end replication problem" and results in a cumulative shortening of telomeres over many cell divisions. Telomerase can address the end replication problem and thereby maintain telomere lengths constant, but the catalytic subunit (h-TERT in humans) of telomerase is normally not expressed in most somatic (body) cells, which allows the eventual widespread development of aging at the cellular level.

Another key factor besides telomere length is telomere damage, which can produce effects similar to telomere shortening. Telomerase can also repair damaged telomeres, and therefore even levels of telomerase that do not cause telomere lengthening may be therapeutic. This argues in favor of the potential value of even weak telomerase inducers. Weak telomerase inducers might also be safer from the point of view of controlling cancer (see below).

Powerful evidence now suggests that telomere shortening and/or telomere damage can drive aging in non-dividing cells as well. Recent evidence has even linked mitochondrial aging to telomere shortening [2]. Cancer-resistant mice whose telomeres have been elongated live 40% longer than those without telomere elongation [3], and major aging changes induced in mice by telomere shortening, including brain shrinkage and loss of sensory perception, are robustly reversed when telomerase is induced [4]. In humans, life expectancy has been linked to the length of telomeres in blood samples [5]. Therefore, the ability to retain normal healthy telomeres is emerging as a major factor for the control of aging in all somatic cells and in the body as a whole.

Telomerase expression can be induced in cancer cells as the direct or indirect result of genetic damage and can allow the cancer cells to proliferate to a life-threatening extent. This has led to the misconception that expressing telomerase in normal cells will cause them to become cancerous. This is clearly not the case [1, 6], and, in fact, most embryonic and adult stem cells [7] and certain other adult cells needed for the turnover of rapidly dividing cells in selected tissues express active telomerase and remain non-cancerous for life. However, cells that have been artificially induced or engineered to express telomerase (i.e., cells that have been "telomerized") and that later happen to mutate to a cancerous phenotype may well give rise to cancers that are more difficult to eradicate than usual. For this reason, there is justified widespread caution over the concept of maintaining healthy telomeres as a major approach to the control of aging. Although rapid and "profound" death of cancer cells subjected to telomerase inhibition has been demonstrated [8], and Geron is working toward introducing telomerase inhibitors as anti-cancer agents, it would be desirable to devise a method for maintaining telomeres that minimizes the risk of cancer cell proliferation should cancer arise after telomerization. It would also be desirable to devise a method of telomerization that would allow the induced telomerase expression to be rapidly discontinued should a cancer problem arise, thus potentially simulating the effect of a telomerase inhibitor.

Methods that induce telomerase expression for one cell type should be generally effective for other cell types. The mechanisms responsible for telomerase expression and repression should be universal for all cell types in a given organism, so a method for inducing telomerase one non-postmitotic cell type should be useful as well in other non-postmitotic cells whether they are isolated or reside in tissues, organs, or whole organisms, including humans. In addition, if h-TERT can be successfully induced in human cells by a given intervention, then non-human TERT should generally be successfully induced in non-human cells by the same or by essentially the same intervention. Finally, telomerase induction methods that are effective in living cells are also expected to be effective in and to have valuable uses in the context of cell-free gene expression systems.

SUMMARY OF THE INVENTION

The present invention provides means for activating telomerase expression in vitro and in vivo using a desirably weak expression stimulus that simultaneously inhibits the growth of either pre-existing cancer cells or any cancer cells that could by chance arise during the practice of the invention.

More specifically, it is an aim of the present invention to provide a novel nutritional composition comprising an optimally effective dose or concentration of the dipeptide L-carnosine (LC) and an optimally effective combination of and the simple sugar, L-fucose (LF), for inducing the expression of the mRNA that comprises the catalytic moiety of telomerase (TERT or h-TERT mRNA) and the active telomerase enzyme complex itself. It is also anticipated that LC and LC plus LF will activate the expression of TERT or h-TERT (i.e., induce TERT or h-TERT mRNA expression) in cell-free transcription systems as well and will be a useful tool for studying or controlling expression in these systems.

It is a further aim to provide combinations of LC and LF that result in more expression of TERT or h-TERT mRNA than can be obtained with the same amount of LC alone.

It is a further aim of the invention to extend the range of effective concentrations of LC to concentrations that otherwise would be too low to permit any appreciable induction of TERT or h-TERT mRNA.

It is a further aim of the invention to provide combinations of LC and LF that increase the health of living cells in comparison to the effects of exposure to the same concentration of LC in the absence of LF, as indicated by, for example, increased synthesis of ATP.

It is a further aim of the invention to provide the induction of amounts of telomerase that are sufficiently high to be valuable but sufficiently low to minimize cancer risk.

It is a further aim of the present invention to provide a dosage method and dosage form for LC and LC plus LF that enables the required concentrations for TERT or h-TERT and telomerase activation to be achieved in vivo.

It is a further aim of the present invention to provide a means of telomerase induction that minimizes the risk of developing certain types of cancer and that in addition provides the benefit of directly inhibiting the proliferation of any cancer cells that might arise during the course of the practice of the invention.

It is a further aim of the present invention to provide LC and LC plus LF as an enhancer of other inducers of TERT or h-TERT mRNA or telomerase and other inhibitors of telomere attrition and damage. The LC and LC+LF combinations described herein should have additive or synergistic effects with other protective agents such as vitamin D and pharmaceutical and nutritional telomerase activators being developed at Sierra Sciences, TA Sciences, Geron, and elsewhere. Therefore, use of LC or LC plus LF in combination with other telomerase induction or telomere protection methods falls within the scope of the present invention.

It is a further aim of the present invention to provide LC or LC plus LF as a supplement for the culturing of cells and/or tissues in vitro to increase the level of TERT or h-TERT expression or to increase the activity of the telomerase enzyme or to increase the replicative capacity of the treated cells and/or tissues or to cause a reversion of the senescent phenotype to a non-senescent phenotype of the treated cells and/or tissues or to achieve any combination of these desirable effects. The realization of this aim could have considerable investigative, therapeutic, and/or industrial value.

In the present specification and in the claims hereof, it is to be understood that reference to h-TERT or h-TERT mRNA is not intended to be limiting for the scope of the invention, but is intended to include also TERT or TERT mRNA (telomerase reverse transcriptase for non-human species and its mRNA) within the scope of any mentioned or claimed application. Although our experiments involve the specific examination of h-TERT, it is believed that our results are general and apply to non-human species as well.

DETAILED DESCRIPTION OF THE INVENTION

Figure 1:
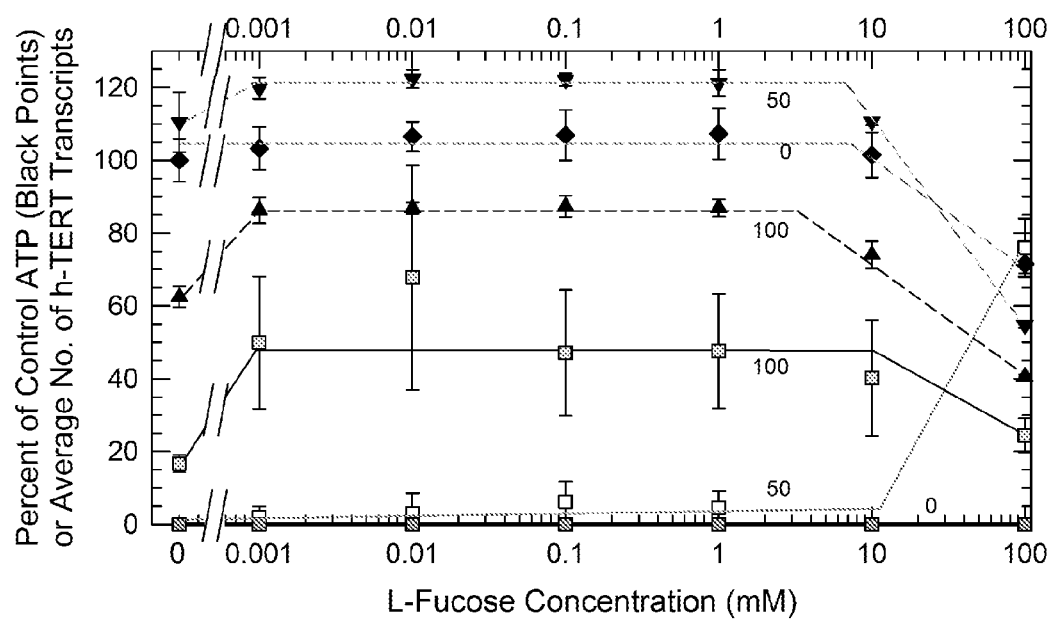
FIG. 1 shows the results of experiment 1 demonstrating the induction of human telomerase catalytic component (h-TERT) mRNA in cultured fibroblasts by LC and combinations of LC and LF and the effects of LC and LC plus LF on ATP levels in these cells.

The invention provides effective concentrations of LC for the induction of h-TERT expression in living cells and a combination of LC and LF that a) increases the expression of h-TERT that would otherwise be achieved by LC alone, or b) reduces metabolic inhibition that would otherwise by caused by LC alone, or c) allows an effective h-TERT expression response to LC to be achieved at a reduced concentration or dose of LC, or d) achieves any combination of a)-c). The best mode concentrations for LC alone are about 50 mM to 100 mM, or more preferably about 51-100 mM or 51-90 mM, and the best mode concentrations for LC in the presence of LF are about 40 mM to about 100 mM or more preferably about 40 to about 90 mM, while the optimal concentration range for LF in the presence of LC ranges from about 1 micromolar to about 100 mM or, more preferably, about 0.1 mM to about 70 mM.

Effective concentrations of LC or LC plus LF are best provided by means that depend upon how the LC or LC plus LF are to be used.

LC or LC plus LF can be provided by external application of a biologically compatible solution, cream, lotion, gel, linament, shampoo, sunscreen, ointment, eyedrop preparation, toothpaste, skin patch, swab, transdermal iontophoresis solution, suppository, lozenge, mouthwash, ear wash, eye wash, nasal lavage solution, or similar external delivery vehicles that contain LC or LC plus LF at their effective concentrations for delivering these agents to the targeted cells at the desired final concentrations. One way of constituting such vehicles is to incorporate LC or LC plus LF at the same molar concentrations (moles per liter of vehicle) in the vehicle medium as is intended to be achieved in the targeted cells, or at somewhat higher concentrations in anticipation of dilution of the applied agents as they enter the targeted tissues and the cells thereof.

Internal application of LC or LC plus LF can be accomplished in the form of a suitable beverage, ingested liquid, seltzer, powder, tablet, pill, lozenge, or similar standard oral dosage form or in the form of a parenteral formulation (e.g., injectable solution, intravenous or intra-arterial solution), instillation or infusion solution (e.g., for infusion into bone, for intrathecal administration, or for subcutaneous instillation), timed release formulation or device, or other suitable means recognized in the art, for delivery into the body, either at the final desired concentrations or at higher concentrations calculated to provide the final desired concentrations at the cellular and/or tissue targets of the administration.

In vitro application of LC or LC plus LF can be accomplished by direct incorporation of LC or LC plus LF into one or more cell/tissue culture or gene expression media, by incorporation into culture media of delayed-release means such as microemulsified, liposomal, micellar, or other timed-release preparations of LC or LC plus LF, or by addition to culture media of concentrated, powdered, microemulsified, liposomal, micellar, timed-release, or other recognized additive forms containing LC or LC plus LF. These application means can be designed to deliver either the final desired concentrations or higher local concentrations calculated to provide the final desired concentrations at the cellular or tissue or acellular targets of the administration after dilution into the environment of the target of LC or LC plus LF administration.

LC, which has been found by us for the first time to increase h-TERT mRNA expression, also has the ability to strongly inhibit the growth of various kinds of cancer cell in vivo at concentrations that are lower than the minimum concentration of LC contemplated for use in the invention [9], and LC also suppressed ATP levels in the cancerous NIH3T3-HER2/neu cells [9] far more than in the noncancerous BJ fibroblasts discussed below, both of which effects make LC a particularly attractive potential agent for reversibly controlling telomere health. The invention consequently provides a novel means of inducing TERT/h-TERT/telomerase expression while simultaneously suppressing the growth of cancer cells.

LC has been shown to have interesting effects in vitro that are superficially consistent with the possible utility of this nutrient for TERT/h-TERT/telomerase induction. In particular, it has been repeatedly shown to reverse the senescent cellular phenotype in culture [10, 11] and to extend the replicative lifespan [10-12]. However, these effects have been consistently attributed by their investigators to factors such as reduced glycation and reduced free radical activity, given that carnosine can inhibit both glycation and reactive oxygen species [10], or to effects on protein metabolism [11], and were never suggested to arise from induction of telomerase activity. And interestingly enough, our own data show that the maximum dose of LC used in these earlier studies (50 mM) is insufficient to induce any h-TERT mRNA unless LF is simultaneously present. It is possible that the TERT gene in the cells used by the earlier investigators was more responsive to LC than the h-TERT gene is in our cells, but the fact remains that this possibility was never contemplated by these investigators or anyone else prior to the hypothesis of one of us (GMF) that LC can induce h-TERT mRNA and prior to our proof that this hypothesis is correct.

A report from China also showed that LC can slow telomere shortening and protect telomeres from damage [12]. This caused the authors of a recent popular book [13] to speculate that carnosine might activate telomerase expression, but the Chinese paper did not show that LC actually increases h-TERT mRNA expression or the activity of the complete telomerase enzyme. Furthermore, the book incorrectly taught that only small amounts of carnosine are needed (the amounts found in an ordinary diet, which are shown herein to be completely inadequate for inducing h-TERT expression). This error demonstrates that the utility of LC for h-TERT mRNA induction depends on knowing the correct dosage range for obtaining a positive effect. The cited book also taught that carnosine is far from the first choice of nutrient for protecting telomeres, many other nutrients being suggested ahead of LC even though none of these other nutrients are believed by either the authors of the book or by the scientists who have studied them to have any telomerase-inducing or -activating activity. Instead, nutrients and lifestyle factors that slow telomere shortening have always been believed to do so by slowing the rate of cell division or reducing direct damage to telomeric DNA, which is completely different from inducing telomerase activity.

We showed for the first time that L-carnosine directly increases h-TERT expression in fibroblasts in 2010 and obtained evidence that it causes the appearance of telomerase activity in 2011. These are exciting findings, particularly given the additional fascinating property of LC of inhibiting the growth of cancer cells in vivo [9].

LC has been widely consumed by health-conscious people for many years, and has not been reported to entail any significant health risks, including cancer. In fact, dePinho has shown that the risk of all adult-onset forms of cancer is increased by telomere shortening [14]. Therefore, LC and LC+LF should reduce the risk of development of cancer and, since they induce h-TERT mRNA only weakly in comparison to the levels of induction seen in cancer cells (based on our estimates, ~1% of the induction prevailing in HeLa cells, as one example), then if cancer should arise, its virulence is very likely to be no worse than it would have been without LC or LC+LF treatment prior to the development of cancer. This is a tremendous advantage of weak telomerase inducers in this era of uncertainly over the possible drawbacks of use of strong telomerase inducers due to concerns over cancer risks.

However, high concentrations of LC are needed to induce h-TERT and telomerase and to reverse the senescent phenotype in vitro, and it is difficult to attain high concentrations in the body. We explored LF to determine whether it might allow LC to be active or more active at lower and more attainable concentrations.

Example 1

Application of LC and LC+LF to Skin

Telomere shortening is expected to have many effects in the body, but perhaps the most visible effects are expected to be in the skin Telomere shortening results in a change in phenotype on the part of dermal fibroblasts, which stop producing the collagen that is required to maintain skin suppleness and instead begin to produce collagenase and elastase, which are enzymes that degrade collagen and another major structural protein in skin, elastin. Telomere shortening also causes fibroblasts to become enlarged and to change their shapes. It is easy to envision how these changes could contribute to visible signs of facial aging.

For these reasons, and because skin is a uniquely accessible part of the body, one of us (GMF) experimented with a variety of skin creams containing LC or LC plus LF to determine whether signs of dermal aging could be reduced by direct application of the cream to skin. It was found that a skin cream comprising 100 mM LC (0.1 mole per liter of cream) in a suitable standard cream base (in this specific case, Banana Boat sunscreen, SPF 30-50, but any known or biologically appropriate skin or facial cream will be effective in delivering LC and LC plus LF into the skin), after 3-4 days, reversed significant wrinkling and that the anti-aging effect of the cream persisted for 3 days or longer after discontinuing the cream. The cream containing LC was initially applied to the left side of the face and compared to the right side of the face, which received only control cream not containing LC. The left side initially had more wrinkles than the right side but, over time, had fewer and less pronounced wrinkles, presumably due to fundamental reversal of dermal aging due to local telomerase reactivation in the skin.

This reduction to practice was accomplished in 2010 and before and was further refined in 2011 using a combination of 100 mM LC and 70 mM LF. The latter formula had similar effects, and volunteer users of the latter formula noticed that their skin felt more smooth and supple with better texture and firmness, diminished fine lines, and reduced pore sizes. This experience also showed that both LC and LF are transported into the skin along with the rest of the cream, no powdery residues of unabsorbed LC or LF being observed after cream absorption.

The analysis provided below provides additional options for LC and LC plus LF administration to, for example, the skin of the face and body that are believed to be even more efficacious. Also, use of 100 mM LC was sometimes seen to cause a short-term pro-wrinkling effect that may be due to osmotic effects of such a high concentration of LC or LC+LF, suggesting that a lower total osmotic concentration (total molar concentration of LC+LF) might have the advantage of reducing or avoiding this minor but important transient effect.

A skin cream, either for facial skin or skin elsewhere on the body, that can reverse skin aging is expected to have significant commercial appeal. It has the great advantage of allowing the target cells to experience very nearly the concentrations intended, at least transiently, since the active substances can be applied to the skin directly. It is also expected to have an advantage over competing creams or hydrating agents in terms of the relatively long persistence of its effects and the fact that it acts by making the skin cells biologically younger rather than acting through a cosmetic effect only.

Example 2

Muscle

Muscles contain high concentrations of LC. One of us (GMF) has ingested oral LC in amounts ranging from 2-8 grams/day and has noticed no side effects and no diminution in muscle strength out to the age of nearly 62 and, in conjunction with a weight training program, is believed to be as strong as or stronger than he has ever been. We speculate the orally administered LC is absorbed and taken up by cells, thereby protecting them from aging, and that LC plus LF may act in a similar way, enhancing the effects of LC.

Thus, although it is difficult to bathe cells in high concentrations of LC and LF in vivo, some key cells may concentrate at least LC and allow telomere protection in this way. Cell membrane LF transporters are also known to exist.

In the best mode, the most effective oral dosage regimen is believed to be 1-9 grams 1 to three times per day, or, more preferably, 2-7 grams 1 to three times per day, with or without the inclusion of LF.

Example 3

Gastrointestinal Tract and Kidneys

It is possible to bathe the cells of the GI tract and, as noted, the skin, in high enough concentrations to achieve a potential telomere-protecting effect. The contents of the human stomach have a volume on the order of 400 ml. LC has a mass of 226 g/mole, which means ~4.5 grams contain 20 millimoles. Dissolved in 400 ml, the concentration would be ~50 mM, which is high enough to induce telomerase when and only when LF is present according to our experience with fibroblasts described below. A dose of 6 grams is equivalent to about 66 mM in the stomach and upper intestine, which the present invention discloses to be effective and ideal for TERT and h-TERT induction with and without LF. A dose of 9 grams is equivalent to about 99 mM in the stomach and upper intestine, which is at the upper limit of the preferred concentration range for LC. Thus LC and particularly LC plus LF may protect the lining of the gastrointestinal tract against the risk of development of cancer by inhibiting telomere shortening in this area, especially if it is concentrated in the intestinal cells in the process of being absorbed into the body at large.

Experience has shown that ingesting six grams of LC with dinner or three grams of LC with a light breakfast does not produce an apparent laxative effect or any other detectable side effect. Therefore, the best mode use of LC for protecting the GI tract and other structures via oral administration is believed to be to ingest the LC with food, although it is also believed that LC will remain effective if food is not ingested with the LC. In the best mode, the most effective oral dosage regimen is believed to be 1-9 grams 1 to three times per day, or, more preferably, 2-7 grams 1 to three times per day.

LC and LF will also be filtered and concentrated by the kidney, which may allow some protection within the genitourinary tract after administration of LC with or without LF in any of the LC-to-LF ratios provided herein. As for protection of muscles and the GI tract, in the best mode, the most effective oral dosage regimen is believed to be 1-9 grams one to three times per day, or, more preferably, 2-7 grams one to three times per day.

Example 4

First In Vitro Experiment

We carried out three in vitro experiments that, together, defined the dose-response relationships of the invention at the cellular level. The model used in all three examples is the BJ fibroblast, maintained in culture for 48 hours in DMEF-12 medium in the presence of a constant concentration of test agent. This is a fully differentiated cell in which telomerase/h-TERT induction is more difficult than usual, so positive results in this cell suggest that there will be a broad positive response in most other cells, an often stronger absolute response in most "telomerase-competent" cells than we observed in BJ fibroblasts, and a perhaps stronger response in many other non-postmitotic cells in the body. Experiments with shorter exposure times to other telomerase inducers suggest that the time of exposure is not a strong factor in the results obtained, and the face cream experiments cited above suggest that even transient exposure is sufficient to induce TERT/h-TERT/telomerase, and, in fact, may be less likely to have negative side effects.

In the first in vitro experiment (Experiment 1), BJ fibroblasts were exposed to 0, 50, and 100 mM carnosine in the presence and absence of LF, the effects of LF being studied independently of and in combination with LC. The results are shown in FIG. 1.

FIG. 1 makes the following points clear.

First, LF is not able to induce h-TERT by itself at any studied concentration (heavy baseline labeled "0" and connecting the dark gray boxes representing 0 mM LC).

Second, even one micromolar LF can augment the induction of h-TERT that is otherwise induced by 100 mM LC.

Third, 50 mM LC appears to increase ATP synthesis by our fibroblasts (dashed line labeled 50 for 50 mM LC; black inverted triangle at zero LF concentration), but the combination of 50 mM LC and a wide range of LF concentrations consistently raised ATP levels even more, to about 20% above control levels, and only very high concentrations of LF in combination with 50 mM LC were able to reduce ATP levels to lower than control values. In contrast, 100 mM LC strongly depressed ATP synthesis in the absence of LF, but the addition of even one micromolar LF eliminated more than half of this effect (yielding a 40% increase in ATP relative to no LF), and only LF concentrations above 10 mM were able to depress ATP synthesis to below what would have been seen with 100 mM LC alone (black triangles).

Fourth, 50 mM LC by itself induces very little h-TERT, even at concentrations up to 10 mM LF, but higher concentrations of LF result in more h-TERT induction by 50 mM LC than can be obtained with 100 mM LC alone or in combination with LF.

Fifth, LF also increases h-TERT expression in the presence of 100 mM LC by approximately 190% (2.9-fold increase) at all concentrations from 1 micromolar LF to 10 mM LF. Even the highest LF concentration did not produce a net inhibition of h-TERT induction by 100 mM LC.

In these experiments, LC+LF was also compared to the Sierra Sciences drug, C0057684, and was found to produce up to about 63% as much induction as this drug (data not shown).

These initial results established the essential basis for the present invention.

In summary, FIG. 1 discloses that a "low" concentration of LC (50 mM) requires high concentrations of LF to significantly induce h-TERT mRNA, whereas high concentrations of LC induce h-TERT better when lower concentrations of LF are used. All but the highest LF concentrations reduced toxicity from LC based on ATP content. The approximate curve fits shown in FIG. 1 were drawn by eye.

Example 5

Second In Vitro Experiment

Figure 2:
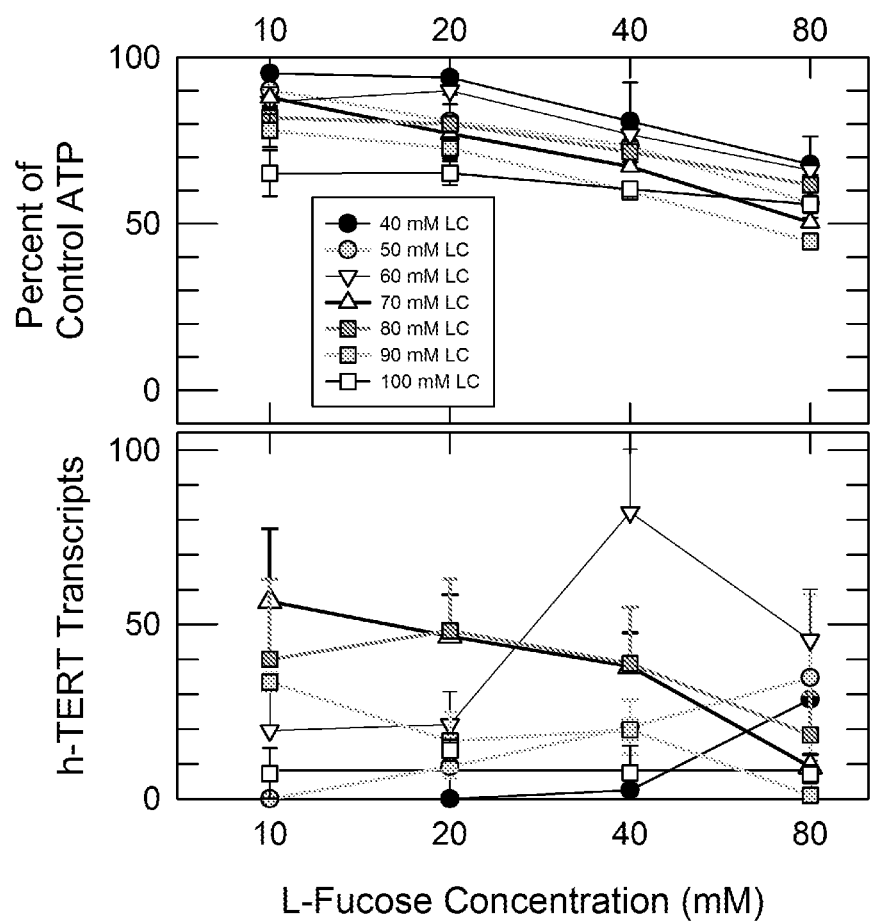
FIG. 2 shows the results of experiment 2 demonstrating the induction of h-TERT mRNA in fibroblasts by LC and combinations of LC and LF and the effects of LC, LF, and LC+LF on ATP synthesis by these cells in culture.

The results of the second experiment are shown in FIG. 2 and provided a closer analysis of the high LF concentration range in view of the remarkable ability of LF to increase h-TERT expression in this range in the case of 50 mM LC and examined a range of LC concentrations between the 50 mM and the 100 mM ranges of FIG. 1, which seem to frame the zone of greatest interest for LC concentrations given minimal h-TERT expression with 50 mM LC at low LF concentrations and significant depression of ATP synthesis by 100 mM LC.

From FIG. 2, we can draw the following conclusions.

First, the previous results showing induction by higher concentrations of LF in the presence of 50 mM LC, with minimal induction at 10 mM LF, were confirmed and extended. Importantly, at 80 mM LF, even 40 mM LC was able to give as good a response to LF as was 50 mM, with slightly less depression of ATP synthesis. This suggests that even 30-40 mM LC can support h-TERT induction in the presence of 50-100 mM LF, such as combinations of 30 mM LC and 60-100 mM LF or 35 mM LC and 60-100 mM LF or 35-40 mM LC and 50-100 mM LF or 35-40 mM LC and 70-90 mM LF.

Second, the inhibitory effect of LF on h-TERT induction seen at 100 mM LC and LF concentrations above 10 mM were seen to switch in between 50 and 60 mM LC, although strong induction seen at 60 mM LC gave excellent results at an LF concentration of 40 mM. At 70 mM LC, the optimal concentration of L F shifted from 40 mM to 10 mM based on this experiment, and the 60LC/40LF and 70LC/10LF combinations both gave absolute results that were better than could be obtained with 80 mM LC at any LF concentration in the range studied. Oddly, although 70 and 90 mM LC showed a linear decline in induction with increasing LF concentration, 80 mM LC did not, but the standard deviations shown are large enough for 80 mM to show the same trend as 70 and 90 mM LC within experimental error.

Third, based on the balance between h-TERT induction and ATP synthesis inhibition, the optimal mixtures are 60 LC and 40-80 LF, 70 LC and 10-40 LF, and 80 LC and 10-40 LF, with the 60/40 mixture being the best overall.

Fourth, in this experiment, the suppression of h-TERT was much more profound at 100 mM LC than seen in the first experiment, again pointing to lower concentrations as being more optimal for this agent. In addition, expression was profoundly suppressed by 80 mM LF in the presence of 80-90 mM LC.

Comparing LC+LF to C0057684 showed that the nutrient combination of LC+LF produced up to about 52% of the induction effect of the drug (data not shown).

Example 6

In Vitro Experiment 3

The third experiment provided a re-analysis of very low concentrations of LF and another more detailed reexamination of the higher LF concentration range. The results are shown in FIGS. 3 and 4.

Figure 3:
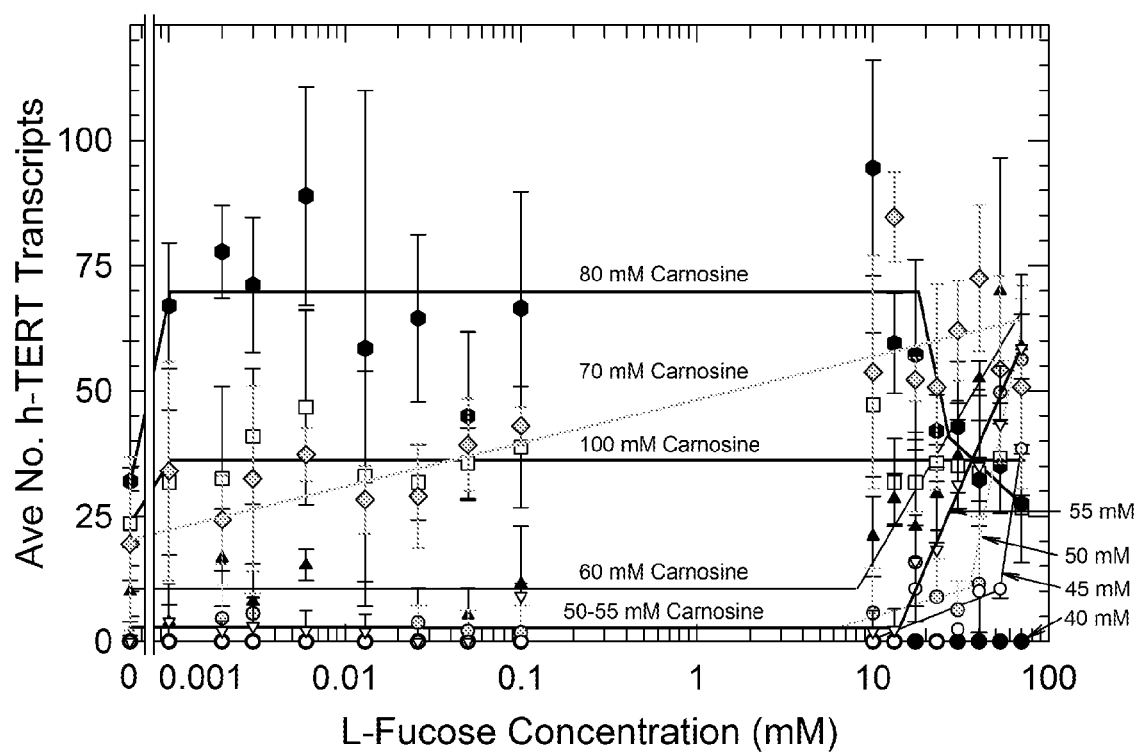
FIG. 3 shows the results of experiment 3 demonstrating h-TERT induction by a large number of combinations of LC and LF.
Figure 4:
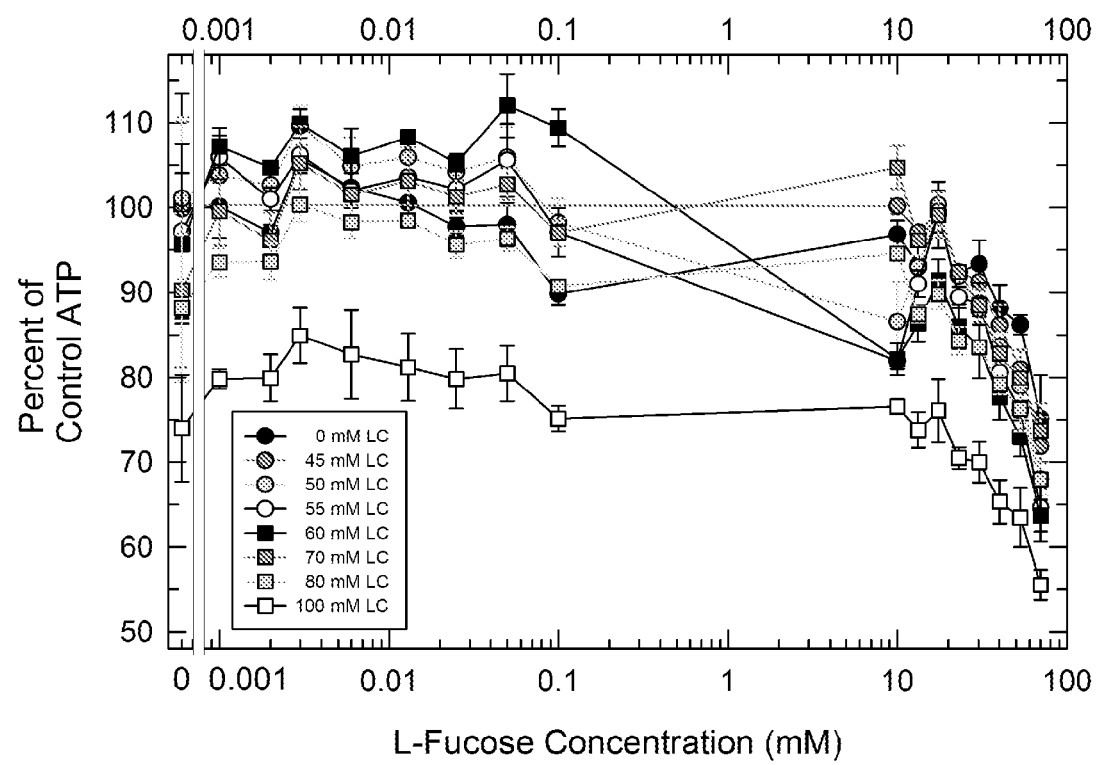
FIG. 4 shows the interaction between LC and LF for the synthesis of ATP production in cultured BJ cells in the third experiment.

In FIG. 3, the following key describes the concentrations of LC represented by the different symbols used: squares, 100 mM LC; hexagons, 80 mM LC; diamonds, 70 mM LC; triangles, 60 mM LC; inverted triangles, 55 mM LC; gray circles, 50 mM LC; white circles, 45 mM LC; and black circles, 40 mM LC. The approximate curve fits shown were drawn by eye. The specific LF concentrations indicated on the x-axis were 0, 0.001, 0.002, 0.003, 0.006, 0.013, 0.026, 0.05, 0.1, 10.025, 13.233, 17.4670, 23.057, 30.435, 40.174, 53.03, and 70.0 mM.

FIG. 3 provides further support for 60-100 mM LC as being the optimum concentration range in the best mode reduction to practice of the invention and confirms the level of induction by 100 mM LC seen in Experiment 1. Inhibition of induction by high LF concentrations was not as great as might have been expected for 100 mM LC, and in this case, did not seem to exist at all. Within statistical error, inhibition at 80 mM LC was seen only at concentrations greater than 23 mM LF, LF concentrations between 1 micromolar and 23 mM giving identical induction of h-TERT amounting to a 119% increase (2.2-fold increase) over the effect of 80 mM LC in the absence of LF. Contrary to the trend shown in Experiment 2, 70 mM LC showed an increasing linear response to the log of the LF concentration over the entire LF concentration range, and the response to 60 mM LC was not limited by, and was in fact strongly enhanced by, the highest concentrations of LF. Overall, the best results were obtained with 60 mM LC at LF concentrations above 23 mM, 70 mM LC at LF concentrations of 10 mM and above, and 80 mM LC at 1 micromolar to 17 mM LF. The response to 80 mM LC was particularly strong in these experiments.

Interestingly, an induction to 40 h-TERT transcripts or more was seen, within experimental variation, for all concentrations of LC from 55 mM-100 mM when the LF concentration was 30-70 mM for each of these LC concentrations (LC/LF molar ratios from approximately 0.78 to 3.33, or ~0.7-4).

Of significant interest FIG. 3, 55 mM LC also yielded more than 50 h-TERT transcripts when 70 mM LF was used, and, remarkably, even 45 mM LC was able to yield as much h-TERT induction as 100 mM LC when 45 mM LC was combined with LF. In addition, the curves were still rising at the maximum LF concentrations tested in this experiment. Therefore, the range of interesting concentrations of LC can be extended downward to as low as at least 45 mM by concentrations of LF above 53 mM, providing further support for LC concentrations as low as 30 mM when combined with higher LF concentrations.

The high-end LF concentrations studied in Experiment 3 were about 10, 13, 17, 23, 30, 40, 53, and 70 mM.

The results obtained are indicative of the utility of different dosage forms of the invention, some emphasizing higher LC and lower LF and others emphasizing higher LF and lower LC. Sustained release formulations are also desirable to keep LC and LF concentrations in their ideal concentration ranges for as long as possible and in an ideal relationship to one another. Of course, in in vitro situations, concentrations can be held steady at any advantageous level.

In the presence and absence of LF, 80 mM seems to be the best single concentration of this agent for h-TERT induction, but in the presence of higher LF levels, experiment 3 indicates that 60-70 mM LC can be very competitive with almost any concentration of LF plus 80 mM, provisionally assuming the very highest responses at 80 mM LC reflect statistical fluctuations. FIG. 4 shows ATP measurements in the third in vitro experiment.

Interestingly, FIG. 4 shows that high and similar ATP levels can be sustained in all concentrations of LC and LF (>60% of controls even at 70 mM LF) except for 100 mM LC. Greater than 80% of control ATP was consistently found for LF concentrations up to 30 mM LF. This further underscores the feasibility of the high-LF formulations tested in the third experiment.

Example 7

Modeling the Effect of Varying Levels of LC and LF

So far, all of the presented data on BJ fibroblasts show results obtained after exposing BJ fibroblasts to constant concentrations of LC and LF for 48 hours. This paradigm provides valid results for industrial applications in which cells may be rejuvenated in vitro, but in vivo, concentrations of both LC and LF will rise and fall with time after administration of a specific dose assuming that continuous administration of LC and LF rather than bolus administration or other means of administration that do not achieve constant target levels of LC and/or LC plus LF is not feasible. In this in vivo context, the net effect of LC and LF administration depends not just on the effects of the concentrations administered and on the peak concentrations achieved (which may be lower than the concentrations administered), but on the effects of the dilutions of the administered concentrations that arise during both the initial absorption and distribution phase, during which concentrations rise to approach and reach the peak achieved concentrations, and the elimination/excretion phase, during which concentrations fall to zero or to a minimum final level that depends upon the frequency or the continuity of dose administration. As noted above, experiments with shorter exposure times to telomerase inducers other than LC and LC+LF suggest that the time of exposure is not a strong actor in the results obtained, and therefore we assume for the sake of further analysis that the effects of transient exposure to LC and to LC+LF are equivalent to the effects of chronic exposure to the same agents at the same concentrations.

Figure 5:
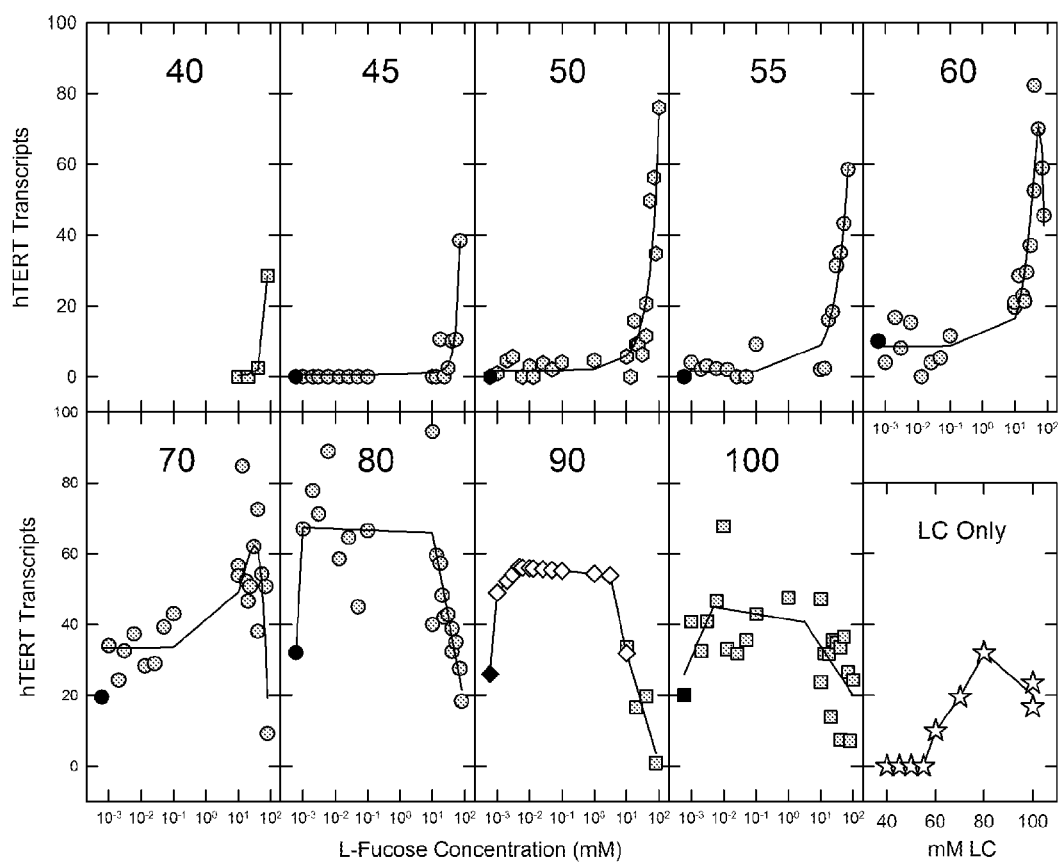
FIG. 5 shows the unified results of all three cell experiments, resolved into 10 dose-effect curves that describe the effect of LF concentration at different LC concentrations and the effect of LC concentration in the absence of LF.

On this basis, in order to accurately arrive at an optimal in vivo dose and combination of LC and LF, the interacting effects of LC and LF on h-TERT mRNA expression were integrated over all concentrations that occur during the entire concentration-time history within the body. To do this, the dose-response curves of the chronic effect of LC and of LC+LF were first determined as a function of LC concentration using pooled data from all three experiments. The raw data were curve-fitted using a combination of 19 different mathematical functions, and the 10 resulting dose-response curves are shown in FIG. 5. The LF dose-response curves are for 9 fixed LC concentrations (indicated at the top of each panel in mM units), and the $10^{th}$ panel shows the LC dose response curve in the absence of LF (stars). In FIG. 5, the black points represent no LF (arbitrarily plotted at $6 \times 10^{-4}$ M LF for convenience). The white points in the panel for 90 mM LC designate an average of the 80 and 100 mM curve fits. The LF concentrations plotted are $10^{-3}$, $2 \times 10^{-3}$, $3 \times 10^{-3}$, $4.8 \times 10^{-3}$, $6 \times 10^{-3}$, $10^{-2}$, 0.013, 0.026, 0.05, 0.1, 1, 3, 3.06, 10, 10.025, 13.233, 17.467, 20, 23.057, 30.435, 40, 40.174, 53.03, 70, 80, 90, and 100 mM (but not all concentrations are plotted in all panels).

Figure 6:
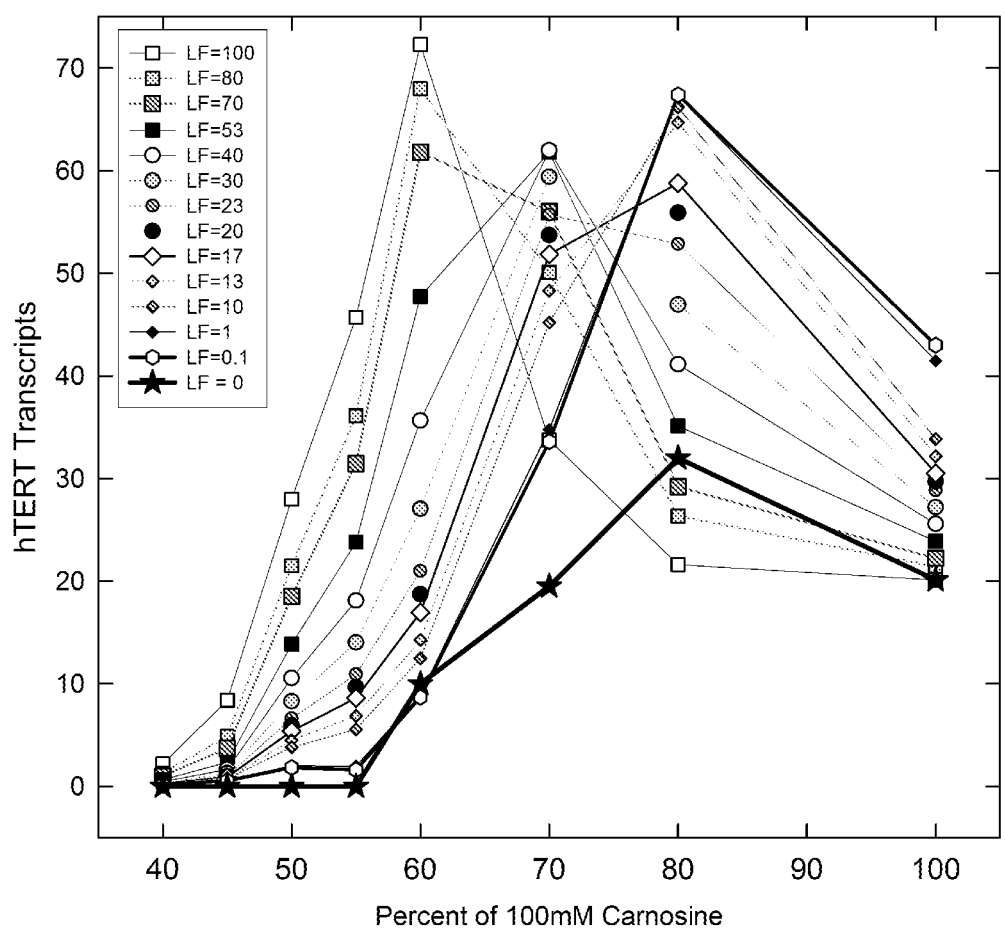
FIG. 6 shows an estimate of how the induction of h-TERT mRNA may change during the rise and fall of LC concentration in an in vivo dosing situation when different concentrations of LF are mixed with 100 mM LC before it is administered.

Using the curves of FIG. 5, the transient effects of LC and of LC+LF during the addition and washout phases of these agents were predicted, and the results are shown in FIG. 6 (the effects at each specific attained concentration would be identical during agent addition as they are during agent washout according to the assumptions of the model). To plot FIG. 6, the concentration of LF was calculated at each LC dilution shown assuming a fixed ratio between LF and LC as both simultaneously rise and fall, and the instantaneous effect of the resulting dilution of LC and LF was calculated from the curve fits of FIG. 5. The effects shown indicate the general course of h-TERT induction expected during the rise and fall in LC concentration that would be expected if a cell, tissue, organ, or human or animal patient were dosed with a combination of 100 mM LC (the assumed peak concentration) and any of the 13 different concentrations of LF ranging from 0.1 mM to 100 mM LF shown in the legend (the initial LF concentrations before dilution) or no LF.

Without LF (stars; heaviest line), remarkably less induction is observed at almost all LC concentrations, in keeping with FIG. 5. The effects of 0.1 and 1 mM LF are remarkably large and are nearly synonymous, in keeping with the flat dose-response curves shown in FIGS. 1 and 3, and concentrations from 1 micromolar to 1 mM are expected to give the same results for the same reason. Clearly, in keeping with FIGS. 1 and 3, the lowest concentration of LF that is active in the current invention is greater than 0 molar but apparently less than 1 micromolar.

The data in FIG. 6 reveal a trimodal interaction between LF, LC, and h-TERT mRNA induction. h-TERT induction rises monotonically with initial LF concentration to a peak at a particular LC concentration and then monotonically declines as LC concentration further increases in every case, but the peak induction effect takes place at different LC concentrations depending on the amount of LF that is present. The peak occurs at 60 mM LC for initial concentrations of ≥70 mM LF, at 70 mM LC for initial concentrations between 20 and 70 mM LF, and at 80 mM LC for initial LF concentrations below 23 mM (20 mM and below).

In order to predict the net effect of each concentration LF, the curves of FIG. 6 were integrated using the trapezoid rule, in essence adding up the induction along each of the FIG. 6 lines over the whole range of LC concentration to enable the sum of induction for each transient concentration to be determined.

Figure 7:
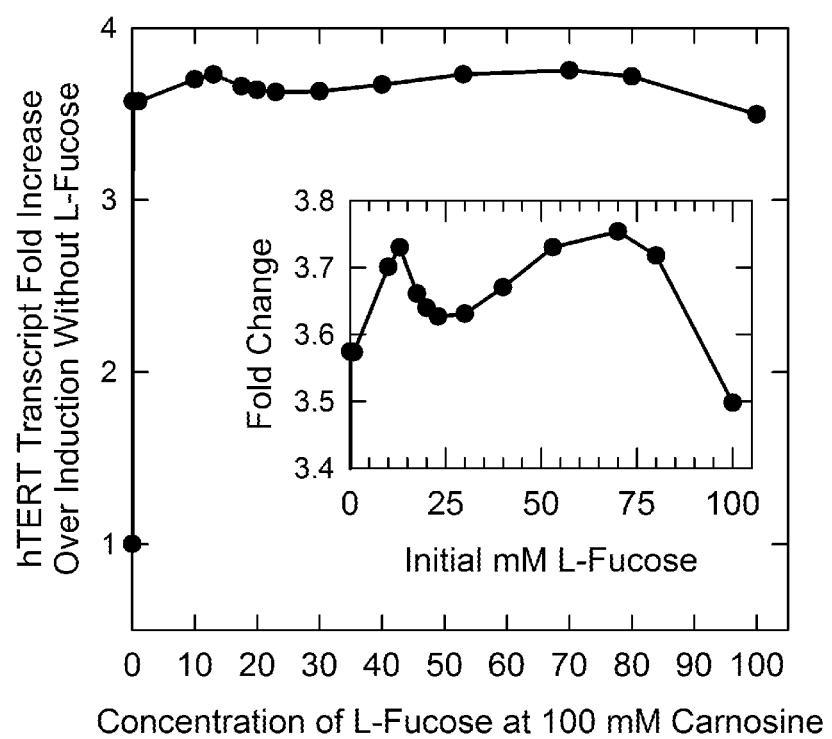
FIG. 7 shows the integral of each curve shown in FIG. 6 plotted against the administered dose of LF and normalized to the integral obtained with no LF.

The results are shown in FIG. 7, and are represented as the expected fold-change in cumulative hTERT mRNA induction caused by the presence of LF during the rise and fall in LC concentration arising during the course of a normal in vivo dosing event when LF is included in the administered dose of 100 mM LC at concentrations of 0 mM to 100 mM LF. For each curve in FIG. 6, the integral was calculated for the transition between each depicted point and the previous depicted point and added to the sum of all previous point-to-point integrals until the complete integral from 40 mM LC through 100 mM LC was obtained. For each coordinate (C2, T2) in FIG. 6, where C2=LC concentration and T2=the number of transcripts at that concentration, the integral 1 between that coordinate and the previous coordinate (C1,T1) was calculated as I=T1*(C2−C1)+0.5×(C2−C1)*(T2−T1)+PI, where PI is the cumulative integral calculated for all previous points through (C1,T1) (the trapezoid rule). The integrals resulting from this process for different initial LF concentrations were divided by the integral resulting from the LF-free curve of FIG. 6 to obtain the fold-change due to LF. Since hTERT mRNA induction during LC and LF introduction should approximately equal the induction during LC and LF washout, the fold-change due to LF would not change significantly by extending the integration to the washout phase.

The main result shown in FIG. 7 is, obviously, that all concentrations of LF drastically increase the effectiveness of LC in raising h-TERT mRNA levels, and that, to a first approximation, the fold-change improvement in induction is actually independent of LF concentration for the most part once the effects over all dilutions of LC and LF are added up. Therefore, the best mode LF concentration for the practice of the invention is remarkably broad, ranging from less than one micromolar (for example, 0.1 micromolar) to 100 mM LF. Accordingly, a composition of matter comprising the combination of 100 mM LC and less than 0.001 mM (e.g., 0.0001 mM) to 100 mM LF, or more preferably the combination of 100 mM LC and 0.001 mM to 90 mM LF (or a molar ratio of LC to LF of 100:0.001 to 100:90), in a suitable vehicle for administration to a cell, tissue, organ, or individual, such as in a biologically compatible solution, lotion, cream, gel, powder, tablet, lozenge, timed release formulation or device, or other dosage form, is a valuable composition for the practice of the present invention. FIGS. 1, 3, 4, and 7 support a dose in the vicinity of 50 micromolar (e.g., 10-100 micromolar) LF as a concentration that, in the presence of 100 mM LC, will minimize the toxicity of the LC+LF mixture while allowing close to a maximum h-TERT mRNA response integral.

But a second-order effect (highlighted in the inset of FIG. 7) is that the integral is technically bimodal, with peaks at 70 and 13 mM LF. The peak at 70 mM LF clearly arises mostly from induction at <80 mM carnosine and from a relatively broad range of LC concentrations over which the peak effect on h-TERT induction is seen for this starting concentration of LF. The peak at 13 mM is clearly due to high induction at ≥80 mM LC and consistently superior induction at <80 mM LC in comparison to lower initial concentrations of LF.

The 13 mM LF peak extends from about 5 to 17 mM LF (a relative range of over three-fold, which on a logarithmic scale is much greater than the 1.6-fold range between the approximately 50 to 80 mM LF limits of the 70 mM LF peak), so a formulation comprising 100 mM LC and 5-17 mM LF, or a molar ratio of LC to LF of 100:5 to 100:17, in a suitable vehicle for administration to a cell, tissue, organ, or individual, such as in a biologically compatible solution, lotion, cream, gel, powder, tablet, lozenge, timed release formulation or device, or other dosage form, is clearly a useful and preferred composition of matter for the invention. More generally, to obtain the largest economic advantage and to avoid potential toxic effects of LF (based on our observations of ATP content), the most preferred concentrations of LF in combination with 100 mM LC are less than 40 mM (e.g., 0.1 micromolar to 30 mM or 0.1 micromolar to 39 mM).

On the other hand, since in a given situation the administration of 100 mM may never result in the achievement of 100 mM LC in the tissue, organ, or individual to whom it is administered, there is a greater certainty of achieving lower rather than higher concentrations of LC, which will reduce concerns over toxicity and favors the higher LF concentration (i.e., a composition of matter comprising the combination of 100 mM LC and 50-80 mM LF, or a molar ratio of LC to LF of 100:50 to 100:80, in a suitable vehicle for administration to a cell, tissue, organ, or individual, such as in a biologically compatible solution, lotion, cream, gel, powder, tablet, lozenge, timed release formulation or device, or other dosage form, is also a preferred composition for the practice of the present invention.)

Attaining the results shown in FIG. 7 requires exposing cells to concentrations of LC and, in some cases, of LF that may, according to FIGS. 1, 2, and 4, have detrimental effects on cells. Reducing the peak concentration of LC to 80 mM or below would reduce the risk of harmful effects on cells, particularly in situations in which the administered dose can be made close to the dose actually achieved in or near the targeted cells, tissues, organs, or organisms. For this reason, the analysis shown in FIGS. 6 and 7 was repeated assuming incorporation of LF into a dosage form of LC containing 60, 70, or 80 mM LC rather than 100 mM LC. To maintain comparability of the resulting integrals, the LC concentrations plotted on the X-axis of the dose-effect curves was, as in FIG. 6, normalized to the highest concentration of LC used in each case and, as in FIGS. 6 and 7, it was assumed that the administered concentration was actually achieved at the targeted cells.

Figure 8:
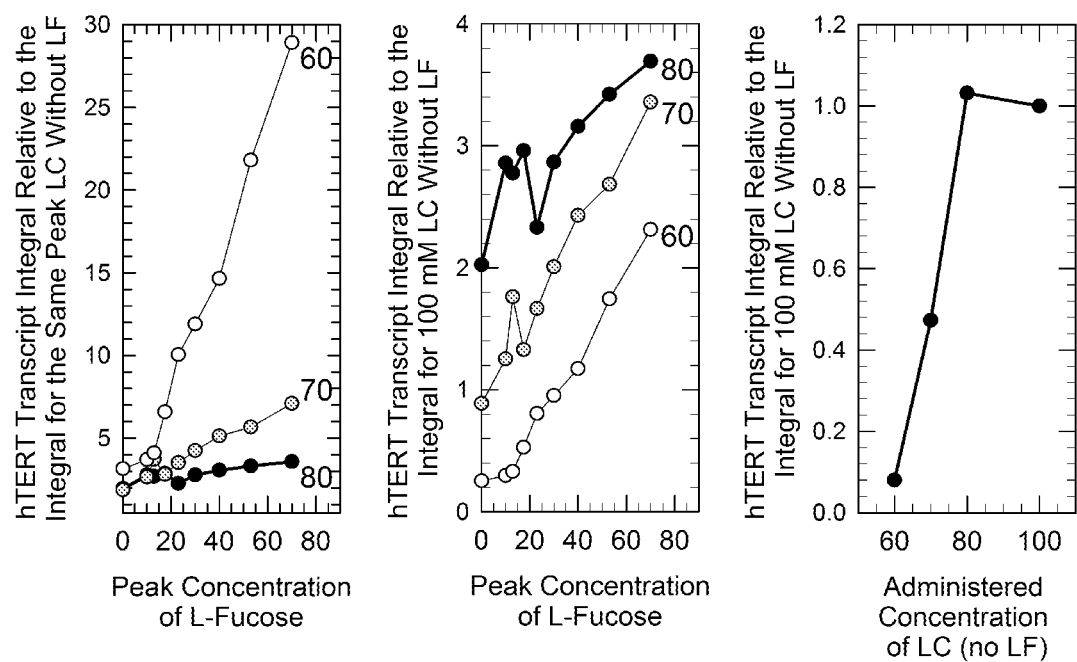
FIG. 8 shows the integral of curves similar to those shown in FIG. 6 when the highest concentration of LC administered is 60-80 mM rather than 100 mM, normalized to either the 100 mM LC integral or to the integrals for each modeled peak LC concentration.

The results of these analyses are displayed in FIG. 8 and indicate the integrated effect of the concentration of LF at the peak LC concentration when the peak LC concentration in the administered dosage form is 60-80 mM (indicated by the labels to the right of each curve in the leftmost two panels). Results are expressed as the effect integral either relative to the effect integral for the same peak LC concentration when LF is not present [left panel; for example for the curve labeled 60, the Y-axis=(integral for the stated initial concentration of LF and 60 mM LC)/(integral for 60 mM LC only)] or relative to the effect integral for 100 mM LC containing no LF (middle panel). Right panel: the integrals for administering 60, 70, 80, or 100 mM LC without LF, expressed relative to the integral for administering 100 mM LC without LF [(integral for initial LC less than 100 mM)/(integral for initial LC=100 mM)].

FIG. 8 shows fold-changes in the response integral due to LF inclusion in the dosage form when fold-change is calculated either on the basis of the effect of LC alone in the dosage form administered or on the basis of the theoretical alternative of dosing with 100 mM LC without LF, ignoring any detrimental effect of the latter on ATP production. Relative to the starting concentration of LC, LF raises the cumulative number of expected h-TERT transcripts by about 2-4 fold when 80 mM LC is administered, by about 2-7 fold when 70 mM LC is administered, and by about 3-29 fold when 60 mM LC is administered (left panel). Relative to what can be achieved using 100 mM LC by itself, LF can allow up to about 2.4 times as many h-TERT transcripts to be produced when 60 mM LC is administered, about 3.4 times as many transcripts when 70 mM LC is administered, and about 3.7 times as many transcripts when 80 mM LC is administered (middle panel). The relationship between the left and middle panels is based on the right panel of FIG. 8, which shows how the h-TERT mRNA induction effect integral depends on the administered concentration of LC. The integral for 80 mM LC is about 3% higher than the integral for 100 mM LC, but the integral for 60 mM LC is only about 8% of the integral for 100 mM LC, with the integral for 70 mM LC falling in between. (To visualize how these results come about, imagine the effect of setting the induction for 80 mM LC in FIG. 6 to 100% of the final LC concentration rather than to 80% of the final concentration before calculating the integral, etc.)

Comparing FIG. 8 and FIG. 4 shows that a combination of 80 mM LC and 10, 20, 40, or 53 mM LF will give an h-TERT mRNA induction response to intermittent dosing that is close to the maximum that can be achieved while maintaining ATP levels at about 95, 90, 80, and 75% of control values, respectively, and therefore combinations of about 70-90 mM LC with about 10-60 mM LF are particularly advantageous. Similarly, 70 mM LC given with 53 or 70 mM LF gives a response integral that is close to the maximum attainable integral with ATP values of about 80 and 73%, respectively, indicating that compositions that combine about 60-80 mM LC with about 45-70 mM LF are also particularly advantageous.

Example 8

Preliminary Evidence of Induction of Telomerase Activity by LC and LC+LF

Preliminary evidence consistent with the induction of telomerase activity by LC and by LC+LF has been obtained using the TRAP assay. Additional work will be required to further define the response.

In summary, the present invention features the following aspects:
1. The use of L-carnosine for the induction of TERT mRNA or h-TERT mRNA in living cells or in cell-free transcription systems, wherein the concentration of L-carnosine administered to or in contact with living cells is higher than 50 mM or wherein said L-carnosine is administered in combination with L-fucose.
2. The use of L-carnosine for the induction of TERT mRNA or h-TERT mRNA in living cells wherein the concentration of L-carnosine administered to or in contact with living cells when L-fucose is not also administered is 51-100 mM.
3. The use of a combination of L-carnosine and L-fucose for the induction of TERT mRNA or h-TERT mRNA in living cells, wherein the concentration of L-carnosine is 30-100 mM and the concentration of L-fucose is 0.1 micromolar to 100 mM.
4. The use of a combination of L-carnosine and L-fucose for the induction of TERT mRNA or h-TERT mRNA in living cells, wherein the concentrations of L-carnosine and L-fucose are 30-100 mM and 1 micromolar to 70 mM, respectively.
5. The use of a combination of L-carnosine and L-fucose for the induction of TERT mRNA or h-TERT mRNA in living cells, wherein the concentrations of L-carnosine and L-fucose are 40-90 mM and 0.1 mM to 70 mM, respectively.
6. The use of a combination of L-carnosine and L-fucose for the induction of TERT mRNA or h-TERT mRNA in living cells, wherein the concentrations of L-carnosine (LC) and L-fucose (LF) are chosen from the combinations consisting of
100 mM LC and 0.0001-100 mM LF;
100 mM LC and 0.001-90 mM LF (or a molar ratio of LC to LF of 100:0.001 to 100:90);
100 mM LC and 70 mM LF;
100 mM LC and 0.1 micromolar to 39 mM LF;
100 mM LC and 10-100 micromolar LF;
100 mM LC and 1 micromolar to 10 mM LF;
100 mM LC and 5-17 mM LF (or a molar ratio of LC to LF of 100:5 to 100:17);
100 mM LC and 50-80 mM LF (or a molar ratio of LC to LF of 100:50 to 100:80);
80 mM LC and 1 micromolar to 17 mM LF;
80 mM LC and 1 micromolar to 20 mM LF;
80 mM LC and 1 micromolar through 23 mM LF;
80 mM LC and 10-40 mM LF;
80 mM LC and 10-53 mM LF;
70-90 mM LC and 10-60 mM LF;
70 mM LC and 10 mM LF;
70 mM LC and 10-40 mM LF;
70 mM LC and 10-70 mM LF;
70 mM LC and 20-70 mM LF;
70 mM LC and 53-70 mM LF;
60-80 mM LC and 45-70 mM LF;
60 mM LC and 23-80 mM LF;
60 mM LC and 40 mM LF;
60 mM LC and 70-100 mM LF;
55-100 mM LC and 30-70 mM LF (LC/LF molar ratios from 0.78 to 3.33 or 0.7-4);
55 mM LC and 70 mM LF;
45 mM LC and 53-100 mM LF;
40 mM LC and 80 mM LF; and
30-40 mM LC and 50-100 mM LF.
7. The use of L-carnosine or a combination of L-carnosine an L-fucose for the induction of TERT mRNA or h-TERT mRNA in living cells, wherein said living cells are exposed to L-carnosine or to said combination of L-carnosine and L-fucose in vitro or in vivo.
8. The use of a combination of L-carnosine and L-fucose for the induction of TERT mRNA or h-TERT mRNA in living cells, wherein the presence of L-fucose increases the induction of TERT mRNA or h-TERT mRNA that would have been caused by L-carnosine alone or reduces metabolic inhibition that would have been caused by L-carnosine alone or allows TERT mRNA or h-TERT mRNA induction at a concentration or dose of L-carnosine that otherwise would not induce h-TERT mRNA or achieves any combination of these effects.
9. The use of L-carnosine for the induction of TERT mRNA or h-TERT mRNA in living cells in vivo, wherein LC is ingested in a dosage form comprising 1-9 grams, or more preferably, 2-7 grams, of L-carnosine with or without the simultaneous presence of L-fucose, 1 to 3 times a day.
10. The use of L-carnosine for the induction of TERT mRNA or h-TERT mRNA in vivo, wherein LC is ingested in a dosage form comprising 1-9 grams, or more preferably, 2-7 grams, of L-carnosine with or without the simultaneous presence of L-fucose, 1 to 3 times per day, and wherein telomere shortening, aging, and/or the risk of cancer development is inhibited in at least one of: the lining of the gastrointestinal tract, muscles, or the kidneys.

11. The use of a combination of L-carnosine and L-fucose for the induction of TERT mRNA or h-TERT mRNA in living cells, wherein the L-carnosine or the said combination of L-carnosine and L-fucose is administered to or brought in contact with living cells in vitro or in vivo via a suitable vehicle for administration to a cell, tissue, organ, or individual, such as in a biologically compatible solution, cream, lotion, gel, linament, shampoo, sunscreen, ointment, eyedrop preparation, toothpaste, skin patch, swab, transdermal iontophoresis solution, suppository, lozenge, mouthwash, ear wash, eye wash, nasal lavage solution, or similar external delivery vehicles or in a suitable beverage, ingested liquid, seltzer, powder, tablet, pill, lozenge, or similar standard oral dosage form or in the form of a parenteral formulation (e.g., injectable solution, intravenous or intra-arterial solution), instillation or infusion solution (e.g., for infusion into bone, for intrathecal administration, or for subcutaneous instillation), timed release formulation or device, or other suitable means recognized in the art, for delivery into the body, in each case so as to deliver L-carnosine or said combination of L-carnosine or L-fucose either at the final desired concentrations or at higher concentrations calculated to provide the final desired concentrations at the cellular and/or tissue targets of the administration or into the body or body region at large. For skin creams, incorporating LC and LF at the molar concentrations in the cream that are intended to be delivered to the cells of the skin is one effective way of constituting the cream.

12. The use of a combination of L-carnosine and L-fucose for the induction of TERT mRNA or h-TERT mRNA in living cells, wherein the L-carnosine or the said combination of L-carnosine and L-fucose is administered to or brought in contact with living cells in vitro or in vivo via a suitable vehicle for administration to a cell, tissue, organ, or individual, wherein the said vehicle incorporates L-carnosine and/or L-carnosine plus L-fucose at the same molar concentrations (moles per unit volume) in the vehicle medium, such as in a non-aqueous skin cream, as is intended to be achieved in the targeted cells, or at somewhat higher molar concentrations (such as, up to two to 10 times the final concentrations intended to be delivered to the targeted cells or to the body) in anticipation of dilution of the applied agents as they enter the targeted tissues or cells.

13. The use of L-carnosine or a combination of L-carnosine and L-fucose for the induction of TERT mRNA or h-TERT mRNA in living cells, wherein the induction of TERT mRNA or h-TERT mRNA is relatively weak in comparison to the levels of induction seen in cancer cells.

14. The use of L-carnosine or a combination of L-carnosine and L-fucose for the induction of TERT mRNA or h-TERT mRNA in living cells, wherein said L-carnosine or said combination of L-carnosine and L-fucose is used as an enhancer of the effects of other inducers of TERT mRNA or h-TERT mRNA or telomerase and/or other inhibitors of telomere attrition and damage or other methods of telomerase induction.

15. The use of L-carnosine or a combination of L-carnosine and L-fucose for the induction of TERT mRNA or h-TERT mRNA in living cells, wherein the enhancement of TERT mRNA or h-TERT mRNA is accompanied by inhibition of the proliferation of potentially cancerous cells by the presence of L-carnosine.

16. The exposure of living cells or tissues in vitro to L-carnosine or a combination of L-carnosine and L-fucose, wherein said exposure increases telomerase activity or increases the replicative capacity of the treated cells or tissues or causes a reversion of the senescent phenotype to a non-senescent phenotype of the treated cells or tissues and wherein said use of L-carnosine or a combination of L-carnosine and L-fucose has investigative, therapeutic, or industrial value.

17. The exposure of living cells or tissues in vitro to L-carnosine or a combination of L-carnosine and L-fucose, wherein said exposure is accomplished by direct incorporation of LC or LC plus LF into one or more cell/tissue culture or cell-free gene expression media, by incorporation into culture media of delayed-release or intracellular delivery means such as microemulsified, liposomal, micellar, or other timed-release or intracellular delivery preparations of LC or LC plus LF, or by addition to culture media of concentrated, powdered, microemulsified, liposomal, micellar, timed-release, or other recognized additive forms containing LC or LC plus LF.

REFERENCES

1. Bodnar, A. G., M. Ouellette, M. Frolkis, S. E. Holt, C.-P. Chiu, G. B. Morin, C. B. Harley, J. W. Shay, S. Lichtsteiner, and W. E. Wright, *Extension of life-span by introduction of telomerase into normal human cells*. Science, 1998. 279: p. 349-352.
2. Sahin, E., Colla S, Liesa M, Moslehi J, Müller F L, Guo M, Cooper M, Kotton D, Fabian A J, Walkey C, Maser R S, Tonon G, Foerster F, Xiong R, Wang Y A, Shukla S A, Jaskelioff M, Martin E S, Heffernan T P, Protopopov A, Ivanova E, Mahoney J E, M. Kost-Alimova, Perry S R, Bronson R, Liao R, Mulligan R, O. S. Shirihai, L. Chin, and R. A. DePinho, *Telomere dysfunction induces metabolic and mitochondrial compromise*. Nature, 2011. 470: p. 359-365.
3. Tomas-Loba, A., I. Flores, P. J. Fernandez-Marcos, M. L. Cayuela, A. Maraver, A. Tejera, C. Borras, A. Matheu, P. Klatt, J. M. Flores, J. Vina, M. Serrano, and M. A. Blasco, *Telomerase reverse transcriptase delays aging in cancer-resistant mice*. Cell, 2008. 135: p. 609-622.
4. Jaskelioff, M., F. L. Muller, J. Paik, E. Thomas, S. Jiang, A. C. Adams, E. Sahin, M. Kost-Alimova, A. Protopopov, J. Cadiñanos, J. W. Horner, E. Maratos-Flier, and R. A. Depinho, *Telomerase reactivation reverses tissue degeneration in aged telomerase-deficient mice*. Nature, 2011. 469: p. 102-106.
5. Cawthon, R. M., K. R. Smith, E. O'Brien, and e. al, *Association between telomere length in blood and mortality in people aged 60 years or older*. Lancet, 2003. 361: p. 393-395.
6. Jiang X R, Jimenez G, Chang E, Frolkis M, Kusler B, Sage M, Beeche M, Bodnar A G, Wahl G M, Tisty T D, and C. P. Chiu, *Telomerase expression in human somatic cells does not induce changes associated with a transformed phenotype*. Nat Genet, 1999. 21: p. 111-114.
7. Marion, R. M. and M. A. Blasco, *Telomeres and telomerase in adult stem cells and pluripotent embryonic stem cells*. Adv Exp Med Biol, 2010. 695: p. 118-131.
8. Kushner, D. M., J. M. Paranjape, B. Bandyopadhyay, and e. al., *2-5A antisense directed against telomerase RNA produces apoptosis in ovarian cancer cells*. Gynecol Oncol, 2000. 76: p. 183-192.

9. Renner, C., N. Zemitzsch, B. Fuchs, and e. al., *Carnosine retards tumor growth in vivo in an NIH3T3-HER2/neu mouse model. Mol Cancer,* 2010. 9: p, 1-7.
10. McFarland, G. A. and R. Holiday, *Further evidence for the rejuvenating effects of the dipeptide L-carnosine on cultured human diploid fibroblasts.* Exp Gerontol, 1999. 34: p, 35-45.
11. McFarland, G. A. and R. Holliday, *Retardation of the senescence of cultured human diploid fibroblasts by carnosine.* Exp Cell Res, 1994. 212: p. 167-175.
12. Shao, L., Q. H. Li, and Z. Tan, *L-carnosine reduces telomere damage and shortening rate in cultured normal fibroblasts.* Biochem Biophys Res Commun, 2004. 324: p. 931-936.
13. Fossel, M., G. Blackburn, and D. Woynarowski, *The Immortality Edge: Realize the Secrets of Your Telomeres for a Longer, Healthier Life.* 2011, Hoboken: John Wiley & Sons.
14. DePinho, R. A., *The age of cancer.* Nature, 2000. 408: p. 248-254.

The invention claimed is:

1. A method for the induction of TERT mRNA or h-TERT mRNA in living cells or in cell-free transcription systems, comprising contacting said living cells with a concentration of L-carnosine greater than 50 mM or with L-carnosine in combination with L-fucose.

2. The method of claim 1, wherein the concentration of L-carnosine administered to contact said living cells when L-fucose is not also administered is 51-100 mM.

3. The method of claim 1, wherein, in said combination of L-carnosine and L-fucose, the concentration of L-carnosine is 30-100 mM and the concentration of L-fucose is 0.1 micromolar to 100 mM.

4. The method of claim 3, wherein the concentrations of L-carnosine and L-fucose are 40-100 mM and 1 micromolar to 70 mM, respectively.

5. The method of claim 4 wherein the concentrations of L-carnosine and L-fucose are 40-90 mM and 0.1 mM to 70 mM, respectively.

6. The method of claim 3, wherein the concentrations of L-carnosine (LC) and L-fucose (LF) are chosen from the combinations consisting of
100 mM LC and 0.0001-100 mM LF;
100 mM LC and 0.001-90 mM LF;
100 mM LC and 70 mM LF;
100 mM LC and 0.1 micromolar to 39 mM LF;
100 mM LC and 10-100 micromolar LF;
100 mM LC and 1 micromolar to 10 mM LF;
100 mM LC and 5-17 mM LF;
100 mM LC and 50-80 mM LF;
80 mM LC and 1 micromolar to 17 mM LF;
80 mM LC and 1 micromolar to 20 mM LF;
80 mM LC and 1 micromolar through 23 mM LF;
80 mM LC and 10-40 mM LF;
80 mM LC and 10-53 mM LF;
70-90 mM LC and 10-60 mM LF;
70 mM LC and 10 mM LF;
70 mM LC and 10-40 mM LF;
70 mM LC and 10-70 mM LF;
70 mM LC and 20-70 mM LF;
70 mM LC and 53-70 mM LF;
60-80 mM LC and 45-70 mM LF;
60 mM LC and 23-80 mM LF;
60 mM LC and 40 mM LF;
60 mM LC and 70-100 mM LF;
55-100 mM LC and 30-70 mM LF;
55 mM LC and 70 mM LF;
45 mM LC and 53-100 mM LF;
40 mM LC and 80 mM LF; and
30-40 mM LC and 50-100 mM LF.

7. The method of claim 6, wherein the molar ratio of LC/LF is from 100:0.001 to 100:90.

8. The method of claim 1 wherein said living cells are contacted with one or more of L-carnosine and said combination of L-carnosine and L-fucose in vivo.

9. The method of claim 1, wherein the presence of L-fucose increases the induction of h-TERT mRNA that would have been caused by L-carnosine alone or reduces metabolic inhibition that would have been caused by L-carnosine alone or allows h-TERT mRNA induction at a concentration or dose of L-carnosine that otherwise would not induce h-TERT mRNA or achieves any combination of these effects.

10. The method of claim 1 wherein said contacting is in vivo in humans and wherein LC is ingested in a dosage form comprising 1-9 grams of L-carnosine with the simultaneous presence of L-fucose, 1 to three times per day.

11. The method of claim 10 wherein said contacting results in inhibition of one or more of telomere shortening, aging induced by telomere shortening, and the risk of cancer development in one or more of the lining of the gastrointestinal tract, muscles, and the kidneys.

12. The method of claim 1, wherein said combination of L-carnosine and L-fucose is administered to or brought in contact with living cells in vivo via a suitable vehicle for administration to a cell, tissue, organ, or individual, in each case so as to deliver L-carnosine or said combination of L-carnosine or L-fucose either at the final desired concentrations or at higher concentrations calculated to provide the final desired concentrations at the cellular and/or tissue targets of the administration or into the body or body region at large.

13. The method of claim 12, wherein said vehicle incorporates one or more of (i) L-carnosine and (ii) L-carnosine plus L-fucose at the same molar concentrations (moles per unit volume) in the vehicle medium as is intended to be achieved in the targeted cells, or at higher molar concentrations (including up to two to 10 times the final concentrations intended to be delivered to the targeted cells or to the body) in anticipation of dilution of the applied agents as they enter the targeted tissues and the cells thereof.

14. The method of claim 12, wherein said suitable vehicle is a biologically-compatible external delivery vehicle comprising one or more of a solution, cream, lotion, gel, linament, shampoo, sunscreen, ointment, eyedrop preparation, toothpaste, skin patch, swab, transdermal iontophoresis solution, suppository, lozenge, mouthwash, ear wash, eye wash, and nasal lavage solution.

15. The method of claim 1 wherein the induction of h-TERT mRNA is relatively weak in comparison to the levels of induction seen in cancer cells.

16. The method of claim 1 wherein said combination of L-carnosine and L-fucose is used as an enhancer of the effects of other inducers of h-TERT mRNA or telomerase and/or other inhibitors of telomere attrition and damage or other methods of telomerase induction.

17. The method of claim 1, wherein the enhancement of h-TERT mRNA is accompanied by inhibition of the proliferation of potentially cancerous cells by the presence of L-carnosine.

18. The method of claim 1 wherein said living cells are exposed to said combination of L-carnosine and L-fucose in vitro and wherein said exposure increases telomerase activity or increases the replicative capacity of the treated cells or causes a reversion of the senescent phenotype to a non-senescent phenotype of the treated cells and wherein said treated cells may reside in tissues.

19. The method of claim 1 wherein said living cells are exposed to said combination of L-carnosine and L-fucose in vitro and wherein said exposure is accomplished by direct incorporation of LC plus LF into one or more cell/tissue culture or cell-free gene expression media, by incorporation into culture media of delayed-release or intracellular delivery means, or by addition to culture media of concentrated, powdered, microemulsified, liposomal, micellar, timed-release, or other recognized additive forms containing LC plus LF.

20. The method of claim 1, wherein said contacting is in vivo in humans and wherein LC is ingested in a dosage form comprising 2-7 grams of L-carnosine with the simultaneous presence of L-fucose, 1 to three times per day.

* * * * *